United States Patent [19]

Christensen

[11] Patent Number: Plant 6,151

[45] Date of Patent: Apr. 19, 1988

[54] HYBRID TEA ROSE PLANT CV. AROVULUC

[75] Inventor: Jack E. Christensen, Ontario, Calif.

[73] Assignee: Armstrong Nurseries, Inc., Somis, Calif.

[21] Appl. No.: 689,993

[22] Filed: Jan. 9, 1985

[51] Int. Cl.[4] ..... A01H 5/00

[52] U.S. Cl. ..... Plt./11

[58] Field of Search ..... Plt. 11

*Primary Examiner*—Robert E. Bagwill

*Attorney, Agent, or Firm*—William H. Elliott, Jr.; William T. King

[57] ABSTRACT

A new hybrid tea rose for garden decoration, having as its seed parent an undisseminated seedling from the cross [Camelot (Plant Pat. No. 2371)×First Prize (U.S. Plant Pat. No. 2,774)] and as its pollen parent Gingersnap (U.S. Plant Pat. No. 4,330). The new cultivar produces extremely abundant, large, well-formed flowers having an unusual chatoyant coloration of coral orange blushing to deep red. The plant is able to withstand hot climates without a drastic decrease in bloom production or flower size. The new variety is an attractive, round, bushy plant of medium height with vigorously growing, dark green foliage.

1 Drawing Sheet

This invention relates to a new variety of hybrid tea rose cv. Arovulc. The plant is a medium-height, hardy outdoor seedling of the bush type, cultivated for garden decoration. It was discovered by Jack E. Christensen in Ontario, Calif., and has as its seed parent an undisseminated seedling of the cross [Camelot (U.S. Plant Pat. ·No. 2,371)×First Prize (U.S. Plant Pat. No. 2,774)], and as its pollen parent, Gingersnap (U.S. Plant Pat. No, 4,330).

The new variety cv. Arovulc may be distinguished from other presently available commercial rose cultivars by the following combination of characteristics: its unusual chatoyant flower coloration of coral orange blushing to deep red, essentially as described and illustrated herein; its extremely abundant production of large, well-formed flowers; its attractive, rounded, bushy mature habit; its profusion of dark green foliage that attractively clothes the entire plant; and its ability to withstand hot climates without a drastic decrease in bloom production or flower size. Arovulc holds these distinguishing characteristics through succeeding propagations by budding.

The new rose may be distinguished from its seed parent, an undisseminated seedling of the cross Camelot×First Prize, by the following combination of characteristics. Whereas the seed parent produces relatively uniformly and stably colored, medium-pink flowers, Arovulc produces flowers of a chatoyant coloration of coral orange blushing to deep red, essentially as described and illustrated herein. The petals of Arovulc's flowers have a good substance that tolerates changes in weather, whereas the flower petals of the seed parent are of a very poor substance and do not hold up well. Whereas the seed parent has unusually large foliage, Arovulc has moderately sized foliage which is significantly smaller.

Arovulc may be distinguished from its pollen parent, Gingersnap, by the following combination of characteristics: Arovulc produces flowers of the chatoyant coloration described above, whereas Gingersnap produces flowers of a relatively uniform, bright orange coloration. Gingersnap is classified as a floribunda rose, whereas Arovulc is classified as a hybrid tea. Arovulc usually bears its flowers one to a stem, whereas Gingersnap more commonly bears several flowers to a stem. The flowers of Gingersnap are 3½ to 4 inches in diameter, whereas Arovulc bears significantly larger flowers of 4½ to 5½ inches in diameter.

The accompanying drawing illustrates the plant in color and shows the flowering thereof from bud to full bloom. Throughout this specification, color names beginning with a small letter signify that the name of that color as used in common speech is aptly descriptive. Color names beginning with a capital letter designate values based upon the R.H.S. Colour Chart of The Royal Horticultural Society in London, England.

The descriptive matter which follows pertains to roses of the new variety grown in the environment of southern California and is believed to apply to plants of the variety grown in similar conditions of soil and climate elsewhere.

FLOWER

The new variety usually bears its flowers singly, sometimes two or three flowers per stem, in irregular, rounded clusters. Flowers are borne on stems of normal strength that are medium in length for the class. Outdoors, the plant blooms nearly continuously and very abundantly during the growing season. It has a slight tea fragrance.

BUD

The peduncle is of average length for the class and of average caliper, strong and erect. It is moderately rough, with numerous stipitate glands and numerous small, soft prickles. The peduncle is between Yellow-Green 146B and Green 137B in color.

Before the calyx breaks, the bud is medium to large in size for the class, medium to long in length, and pointed and ovoid in form. There are a few foliaceous appendages and many stipitate glands on its surface, and there are usually slender, shallowly serrate foliaceous parts extending beyond the tip of the bud, equal to one half or more of its length.

As the calyx breaks, bud color is between Red 42A and Orange-Red 34A.

The inner surface of the sepals has a fine, wooly tomentum; margins are lined with stipitate glands and hairs.

As the first petal opens, the bud is of average size for the class, medium to long in length, and pointed to ovoid in form. The coloration on the outside of the newly-opening petals has a basal attachment zone of new Yellow 9A in color which quickly suffuses to between Red 39B and Orange-Red 35B; areas exposed to sunlight blush to between Red 47A and Orange-Red 34A. Inside, the petals display a basal attachment zone near Yellow 7A in color which quickly suffuses to between Red 39A and Orange-Red 35B; areas exposed to sunlight blush to a color deeper than between Red 46A and Red 47A. The bud opens up well and is not prevented from opening by hot, wet, or dry weather.

BLOOM

When fully open, the bloom is average to large in size for the class, ranging from 4½ to 5½ inches in diameter. Petalage is double, with petals arranged regularly; there are from 25 to 30 petals present and from 1 to 4 petaloids. When half open, the bloom is moderately high-centered in form, and the petals are somewhat spiraled with edges somewhat reflexed outward. When fully open, the bloom is somewhat flat to cupped, with flat to loosely cupped petals and petal edges moderately undulated and reflexed outward.

The petals are of moderately heavy substance and of medium thickness, with insides slightly satiny and outsides slightly shiny to satiny. The outside petals are nearly round to broadly oval in shape with rounded apices. The intermediate petals are nearly round to broadly obovate with rounded apices. The inner petals are narrowly obovate, sometimes irregular, and have rounded apices. Petal colors may be modified by being bordered or shaded or washed or tinted with other colors.

The paragraph immediately following describes the color values observed in a newly opened flower on a plant grown outdoors in Ontario, Calif., in the month of October.

The outside surface of the outside petals has a basal attachment zone near Yellow 9A in color, with the remainder of the petal quickly suffusing to between Red 39B and Orange-Red 35B; areas exposed to sunlight blush to between Red 47A and Orange-Red 34A. The inside surface of the outside petals has a basal attachment zone near Yellow 7A which suffuses to near Red 39A; areas exposed to sunlight coloration of the outside surface of the intermediate and inner petals is the same as the outside surface of the outside petals, except that there is no blushing. The inside surface of the intermediate petals has the same coloration as the inside surface of the outside petals, but with less blushing. The inside surface of the inner petals has the same coloration as the inside surface of the outside petals, but with little or no blushing.

The paragraph immediately following describes the color values observed in a bloom which had been open for three days in the month of October. The plant described had been grown outdoors in Ontario, Calif.

The outside surface of the outside and inner petals has a basal attachment zone near Yellow 4A which quickly suffuses to between Red 47B and Red 41B, with the outer edges blushing to between Red 46A and Red 53A. The inside surface of the outside petals has a basal attachment zone of near Yellow 4A which quickly suffuses to between Red 43C and Red 48C, with areas exposed to sunlight blushing to between Red 46A and Greyed-Purple 183A. The inside surface of the inner petals is the same as the inside surface of the outside petals but with less blushing.

The general color effect of the newly opened flower is between Red 39B and Orange-Red 35B for the inner petals and between Red 47A and Orange-Red 34A for the outer petals. After being open three days, the bloom gives a general color effect that is predominantly between Red 46A and Greyed-Purple 183A. The petals usually drop off cleanly and are not particularly affected by hot, wet, or dry weather. In cold weather, little or no blushing occurs as the flower opens.

In October, flowers on plants of the new variety grown in the garden last on the bush from 3 to 4 days; flowers cut from plants grown outdoors will last from 4 to 5 days at living-room temperatures.

REPRODUCTIVE ORGANS

An average number of stamens are arranged irregularly about the pistils. The filaments are of medium length, and most have anthers. The anthers are of medium size, and all open approximately at once. Anther color is near Yellow-Orange 17C when immature and near Greyed-Orange 166A at maturity. Pollen is moderate in quantity and near Yellow 11B in color.

There are an average number of pistils (approximately 40). The styles are uneven, average to long in length, of thin to average caliper, and somewhat loosely bunched. The stigma is near Red 53B in color.

Under Ontario, Calif. growing conditions, the new variety does not normally set hips.

FOLIAGE

The compound leaves are borne in normal to abundant quantities and usually comprise from three to five leaflets. The leaves are of medium size for the class, moderately heavy to somewhat leathery, and are semi-glossy. The leaflets are nearly oval to ovate in shape, with acute apices and round bases; their margins are irregularly serrate.

The upper surface of the mature foliage is between Yellow-Green 147A and Green 139A in color; its under surface is between Yellow-Green 148C and Green 138B. The upper surface of the young foliage is the same color as the upper surface of the mature foliage, but washed heavily with near Greyed-Purple 187A. The under surface of the young foliage is the same color as the under surface of the mature foliage, but washed heavily with near Greyed-Purple 187B.

The rachis is average to heavy in size, grooved on its upper side, and has some stipitate glands on its edges. The under side of the rachis is extremely hairy and bears stipitate glands.

Stipules are of medium to long length, of moderately narrow width, and have medium-length points turning out at an angle of usually less than 90°.

The plant displays an average resistance to mildew and blackspot as compared to other commercial varieties grown under comparable conditions in Ontario, California.

GROWTH

The plant is much branched, of medium height, and of bushy, upright-spreading habit. It displays very vigorous growth. The canes are of medium caliper for the class.

The main stems are between Yellow-Green 146D and Green 139C in color. They bear few to several large prickles which are of short to medium length for the class. The large prickles are almost straight to hooked slightly downward and have narrow bases of medium length; prickle color is near Greyed-Orange 166D. The main stems bear a few small prickles, also near Greyed-Orange 166D in color, and no hairs.

The branches are of a color between Yellow-Green 146B and Green 137A. They bear several large prickles of short to medium length for the class. The prickles are almost straight to hooked slightly downward, with narrow bases of medium length, and are near Greyed-Orange 166B in color. The branches have a few small prickles near Greyed-Orange 166B in color and no hairs.

New shoots are of the same color as the branches, washed heavily with new Greyed-Purple 187A. They bear several large prickles of medium length for the class, which are almost straight to hooked slightly downward, with moderately long, narrow bases. Prickle color is near Greyed-Purple 187A. There are a few small prickles near Greyed-Purple 187A in color and no hairs.

I claim:

1. The new and distinct variety of rose plant of the hybrid tea class cv. Arovulc and the parts thereof, substantially as shown and described herein, the plant being particularly characterized by its unusual chatoyant flower coloration of coral orange blushing to deep red; its extremely abundant production of large, well-formed flowers; its attractive, rounded, bushy mature habit; its profusion of dark green foliage that attractively clothes the entire plant; and its ability to withstand hot climates without a drastic decrease in bloom production or flower size.

* * * * *

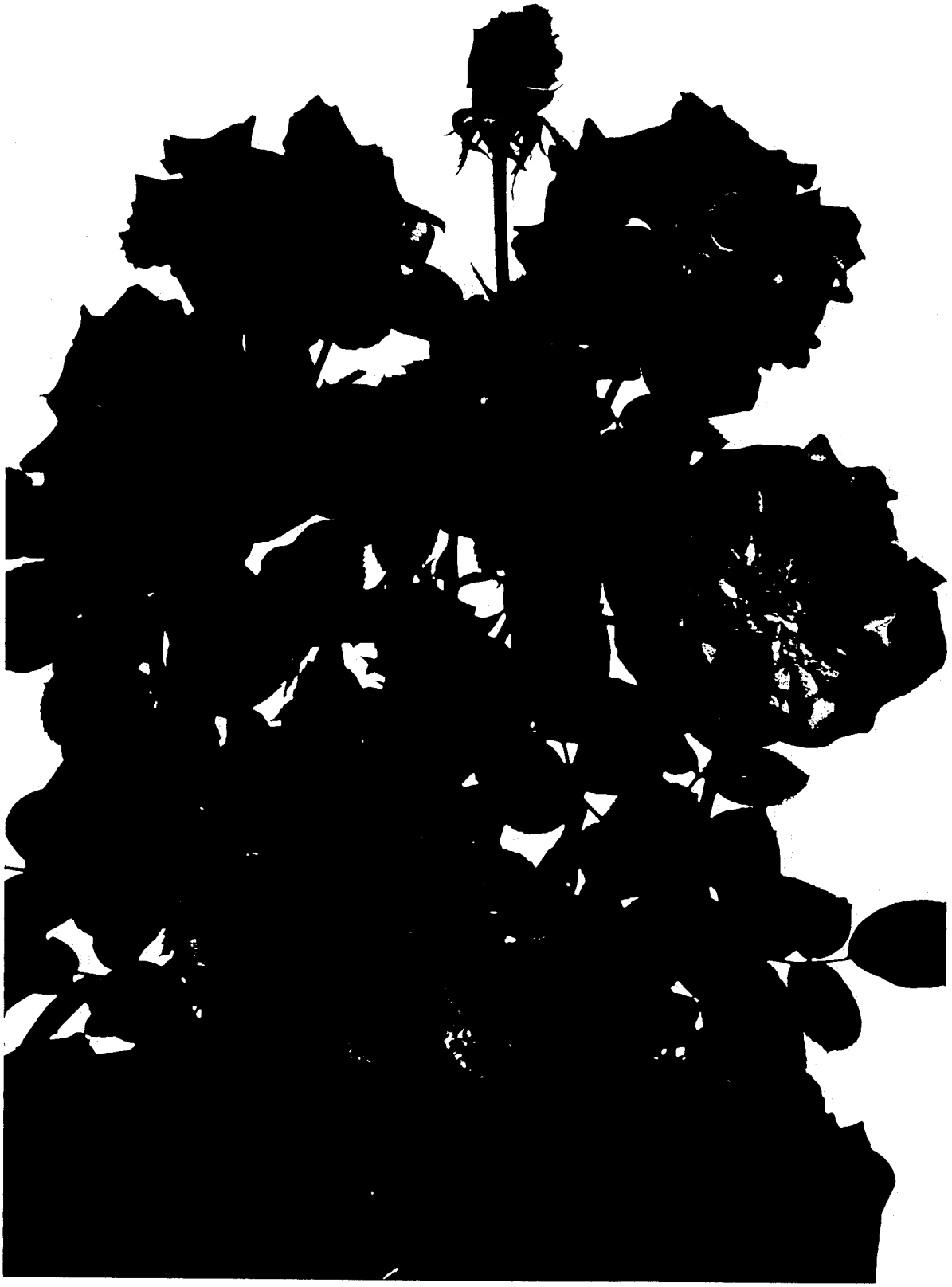

UNITED STATES PATENT AND TRADEMARK OFFICE

CERTIFICATE OF CORRECTION

PATENT NO. : Plant 6,151

DATED : April 19, 1988

INVENTOR(S) : Christensen

It is certified that error appears in the above-identified patent and that said Letters Patent is hereby corrected as shown below:

Title of the patent:
"AROVULUC" should read --AROVULC--.

Signed and Sealed this

Thirteenth Day of September, 1988

*Attest:*

DONALD J. QUIGG

*Attesting Officer*

*Commissioner of Patents and Trademarks*